(12) United States Patent
Trice et al.

(10) Patent No.: US 11,410,752 B2
(45) Date of Patent: Aug. 9, 2022

(54) METHOD OF SYNTHESIZING CHEMICAL COMPOUNDS

(71) Applicants: EMD Millipore Corporation, Burlington, MA (US); Sigma-Aldrich Co. LLC, St. Louis, MO (US)

(72) Inventors: Sarah Trice, Burlington, MA (US); Tim Knehans, Warsaw (PL); Maciej Wojcikowski, Warsaw (PL)

(73) Assignees: EMD Millipore Corporation, Burlington, MA (US); Sigma-Aldrich Co., LLC, St. Louis, MO (US)

( * ) Notice: Subject to any disclaimer, the term of this patent is extended or adjusted under 35 U.S.C. 154(b) by 0 days.

(21) Appl. No.: 16/772,293

(22) PCT Filed: Jul. 30, 2019

(86) PCT No.: PCT/US2019/044068
§ 371 (c)(1),
(2) Date: Jun. 12, 2020

(87) PCT Pub. No.: WO2021/021120
PCT Pub. Date: Feb. 4, 2021

(65) Prior Publication Data
US 2022/0148686 A1    May 12, 2022

(51) Int. Cl.
*G06F 21/60* (2013.01)
*G16C 60/00* (2019.01)
(Continued)

(52) U.S. Cl.
CPC .......... *G16C 60/00* (2019.02); *G06F 21/602* (2013.01); *G06F 21/6227* (2013.01); *G16C 20/90* (2019.02)

(58) Field of Classification Search
CPC ....... G16C 60/00; G16C 20/90; G06F 21/602; G06F 21/6227
See application file for complete search history.

(56) References Cited

U.S. PATENT DOCUMENTS

2001/0018512 A1    8/2001    Blanchard
2005/0033524 A1    2/2005    Cowsert et al.
(Continued)

FOREIGN PATENT DOCUMENTS

WO    WO-2019055499 A1 *    3/2019    ............. G16C 20/10

OTHER PUBLICATIONS

International Search Report and Written Opinion dated Oct. 21, 2019 in corresponding PCT application No. PCT/US2019/044068.
(Continued)

*Primary Examiner* — Meng Li
(74) *Attorney, Agent, or Firm* — Nields, Lemack & Frame, LLC (57) ABSTRACT

A system, software application and method that allows a customer to protect their proprietary database of compounds and substances while utilizing a retrosynthesis software application is disclosed. The customer's proprietary database is encrypted prior to being provided to the retrosynthesis system. This encrypted is performed using a hash and optionally a salt. The retrosynthesis algorithm then creates synthons as is traditionally done. However, after their creation, the synthons are hashed so that they may be compared to the entries in the customer's proprietary database. In this way, the actual contents of the customer's database are never made available to the retrosynthesis system or software application.

18 Claims, 7 Drawing Sheets

(51) Int. Cl.
    *G06F 21/62*     (2013.01)
    *G16C 20/90*     (2019.01)

(56) References Cited

U.S. PATENT DOCUMENTS

| | | | |
|---|---|---|---|
| 2014/0355756 A1* | 12/2014 | Iwamura | H04L 9/0861 |
| | | | 380/30 |
| 2015/0147275 A1 | 5/2015 | Ke et al. | |
| 2019/0007387 A1* | 1/2019 | Jin | G06F 16/951 |
| 2020/0320039 A1* | 10/2020 | Manningham | G06F 16/134 |

OTHER PUBLICATIONS

Coley et al., "Computer-Assisted Retrosynthesis Based on Molecular Similarity", ACS Central Science, vol. 3, pp. 1237-1245, 2017.
Delepine, "RetroPath2.0: A Retrosynthesis Workflow for Metabolic Engineers", Metabolic Engineering, vol. 45, pp. 158-170, 2018.
Libretexts "Chapter 18: Organic Synthesis", Jul. 13, 2016, retrieved from <https://chem.libretexts.org/Courses/Purdue/Purdue%3A_Chem_26605%3A_Organic_Chemistry_ll_(Lipton)/Chapter_18%3A_Organic_Synthesis>.
International Preliminary Report on Patentability dated Feb. 10, 2022 in corresponding PCT application No. PCT/US2019/044068.
Indian communication dated Jun. 27, 2022 in corresponding Indian patent application No. 202117060280.

* cited by examiner

METHOD OF SYNTHESIZING CHEMICAL COMPOUNDS

This application is a National Stage Entry under 35 U.S.C. § 371 of International patent application PCT/US2019/044068, filed Jul. 30, 2019, the disclosure of which is incorporated herein in its entirety.

This disclosure describes systems and methods for synthesizing pathways to create chemical compounds, also referred to as retrosynthetic analysis.

BACKGROUND

Programming a computer to plan multistep chemical syntheses leading to nontrivial targets has been an elusive goal for over five decades. Specifically, one software application, referred to as Synthia™, designed, with minimal human supervision, complete pathways leading to structurally diverse and medicinally relevant targets. These theoretical pathways were subsequently executed in the laboratory, offering substantial improvements over previous approaches or providing the first documented routes to a given target.

Knowing that retrosynthesis is achievable, one can consider expanding the scope of automated retrosynthetic design modalities. One of the interesting possibilities is to allow customers to supply their proprietary database of compounds and to terminate the retrosynthesis when commonly available compounds or compounds from that proprietary database are reached.

However, customers may be reluctant to share their propriety database with another entity, such as the owner of this software application. Therefore, it would be beneficial if there was a system and method for the customer to utilize their proprietary database without allowing other entities to access that database. Further, it would be advantageous if the software application could operate using databases from multiple customers without having access to unencrypted data in any of those databases as well as identifying overlap within these databases.

SUMMARY

A system, software application and method that allows a customer to protect their proprietary database of compounds and substances while utilizing a retrosynthesis software application is disclosed. The customer's proprietary database is encrypted prior to being provided to the retrosynthesis system. This encrypted is performed using a hash and optionally a salt. The retrosynthesis algorithm then creates synthons as is traditionally done. However, after their creation, the synthons are hashed so that they may be compared to the entries in the customer's proprietary database. In this way, the actual contents of the customer's database are never made available in a molecular format to the retrosynthesis system or software application.

BRIEF DESCRIPTION OF THE DRAWINGS

For a better understanding of the present disclosure, reference is made to the accompanying drawings, in which like elements are referenced with like numerals, and in which.

DETAILED DESCRIPTION

Figure 1:
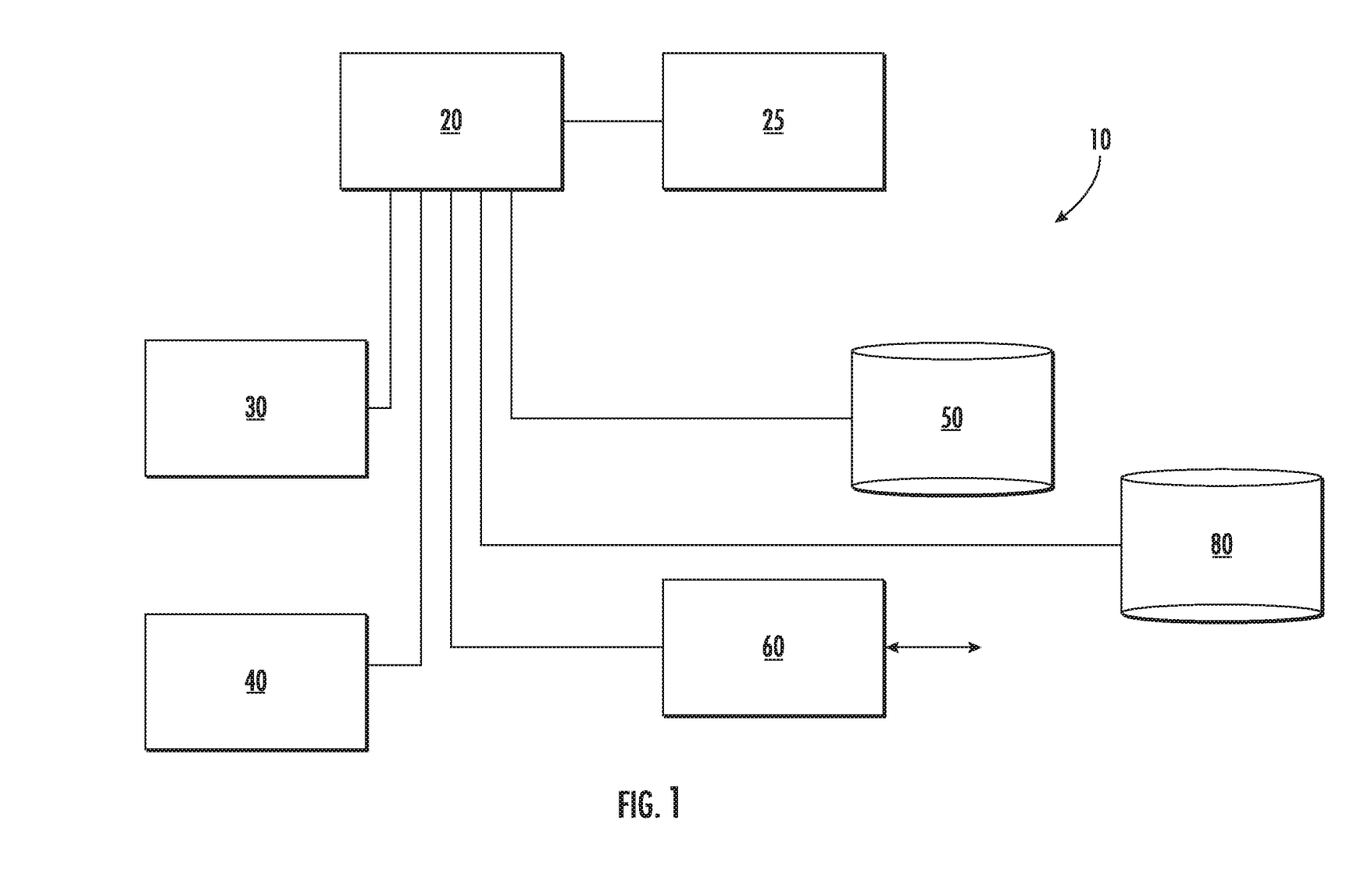
FIG. 1 shows a representative system for performing the retrosynthesis.

The present disclosure represents an advancement in the retrosynthesis of chemical compounds. The present disclosure describes a system, method and software application that allow for retrosynthesis analysis that protects the confidentiality of a customer's library. The software application may be written in any suitable language and may be executed on any system. The software application comprises one or more processing blocks. Each of these processing blocks may be a software module or application that is executed on a computer or other processing unit. A representative retrosynthesis system 10 that executes the software application is shown in FIG. 1. The processing unit 20 can be implemented in numerous ways, such as with dedicated hardware, or with general purpose hardware, such as personal computers, that is programmed using microcode or software to perform the functions recited herein. A local memory device 25 may contain the software application and instructions, which, when executed by the processing unit 20, enable the retrosynthesis system 10 to perform the functions described herein. This local memory device 25 may be a non-volatile memory, such as a FLASH ROM, an electrically erasable ROM or other suitable devices. In other embodiments, the local memory device 25 may be a volatile memory, such as a RAM or DRAM. The retrosynthesis system 10 also comprises a data store 50. The data store 50 may be used to store large amounts of data, such as lists of reaction rules, lists of commercial compounds and their prices per gram. Additionally, the retrosynthesis system 10 may include a user input device 30, such as a keyboard, mouse, touch screen or another suitable device. The retrosynthesis system 10 may also include a display device 40, such as a computer screen, LED display, touch screen or the like. The data store 50, the user input device 30 and the display device 40 are all in communication with the processing unit 20. In some embodiments, the retrosynthesis system 10 may also have a network interface 60, in communication with an external network, such as the internet, which allows the processing unit 20 to access information that is stored remotely from the retrosynthesis system 10.

The data store 50 may store a vast knowledge base of methodologies that describe known reactions. In one embodiment, the data store 50 may include in excess of 70,000 reaction rules. In addition, the retrosynthesis system 10 may have access to diverse collections of starting materials. This information may be stored in the data store 50 or another storage element. Alternatively, this information may be accessible to the processing unit 20 via the network interface 60. In one embodiment, information regarding more than 7 million literature-known substances is available to the processing unit 20. This information may also include pricing per gram for at least some of these substances. Each of these substances may be stored in a text format, as opposed to a graphical format. For example, the substances may be depicted using Simplified Molecular Input Lines Entry System (SMILES) strings. SMILES is a notation that describes the structure of chemical species using ASCII strings. Other notations include IUPAC International Chemical Identifier (InChI), and InChI-Keys. Commonly, regardless of which notation is used, the same compound may be expressed using different strings. Therefore, in certain embodiments, all strings are rewritten using canonical representation.

Additionally, the processing unit 20 has access to a proprietary database 80, which is encrypted. This proprietary database 80 contains the library of compounds and substances that are available to a particular customer of the software application. This proprietary database 80 contains a number of canonical representations, each representation corresponding to a specific substance that is available to that particular user. Each canonical representation is then encrypted using a hash. The hash may be SHA-1, SHA-2, SHA-3, MD5 or another algorithm. The particular hash algorithm is not limited by this disclosure. In certain embodiments, each entry is the proprietary database 80 is salted prior to being hashed. A "salt" is an arbitrary string that is prepended or appended to each canonical representation. This added input further protects the confidentiality of the proprietary database 80.

By salting and hashing the proprietary database 80, a third party would be unable to determine the contents of the proprietary database 80. In this way, a customer may utilize the disclosed retrosynthesis system and software application without providing access to their confidential library of compounds and substances.

Figure 2:
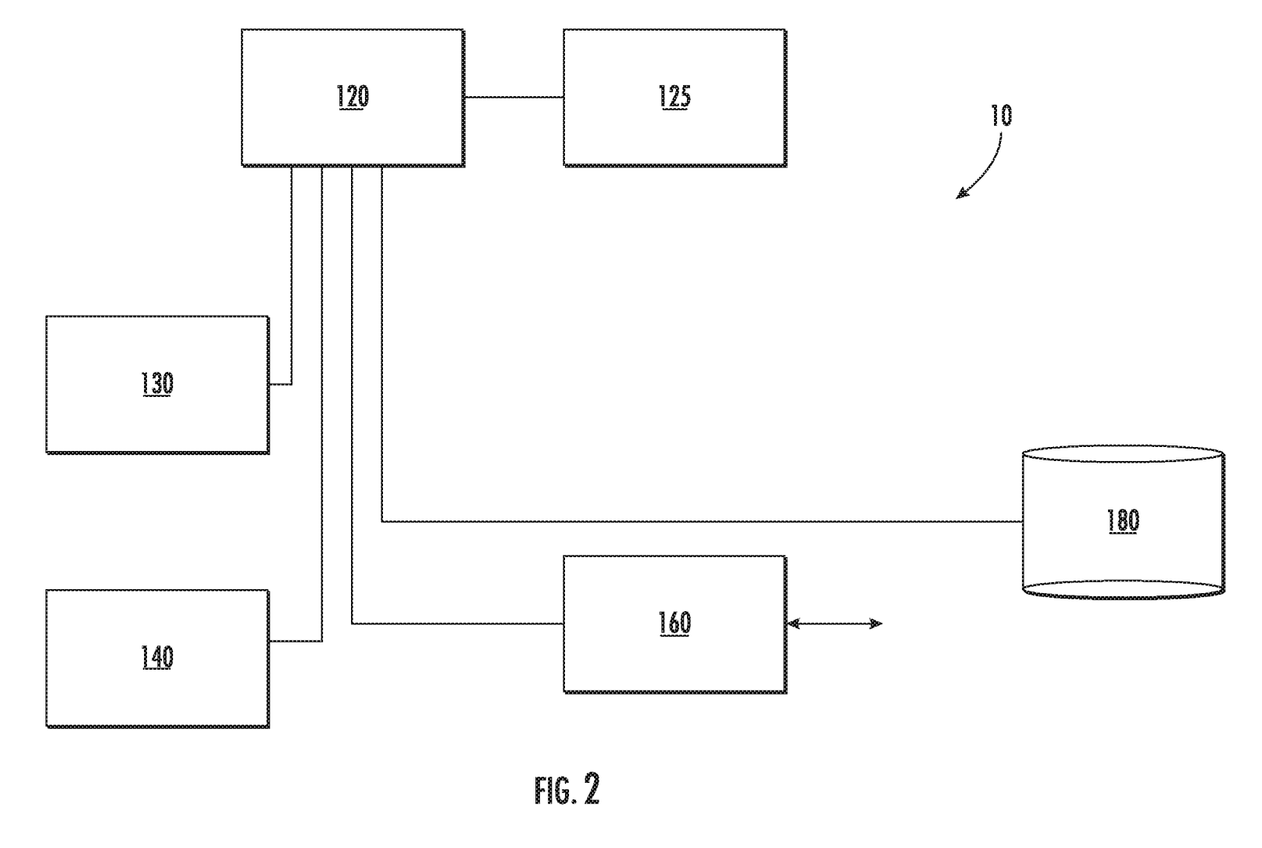
FIG. 2 shows a representative system for a user of the software application described herein.

A representative customer's system 100 is shown in FIG. 2. The processing unit 120 can be implemented in numerous ways, such as with dedicated hardware, or with general purpose hardware, such as personal computers, that is programmed using microcode or software to perform the functions recited herein. A local memory device 125 may contain instructions, which, when executed by the processing unit 120, enable the customer's system 100 to perform the functions described herein. This local memory device 125 may be a non-volatile memory, such as a FLASH ROM, an electrically erasable ROM or other suitable devices. In other embodiments, the local memory device 125 may be a volatile memory, such as a RAM or DRAM. The customer's system 100 may include a user input device 130, such as a keyboard, mouse, touch screen or another suitable device. The customer's system 100 may also include a display device 140, such as a computer screen, LED display, touch screen or the like. The user input device 130 and the display device 140 are all in communication with the processing unit 120. In some embodiments, the customer's system 100 may also have a network interface 160, in communication with an external network, such as the internet, which allows the processing unit 120 to provide its proprietary database to the retrosynthesis system 10.

The customer's system 100 may also have a data store that contains the customer's database 180 of compounds and substances.

Figure 3:
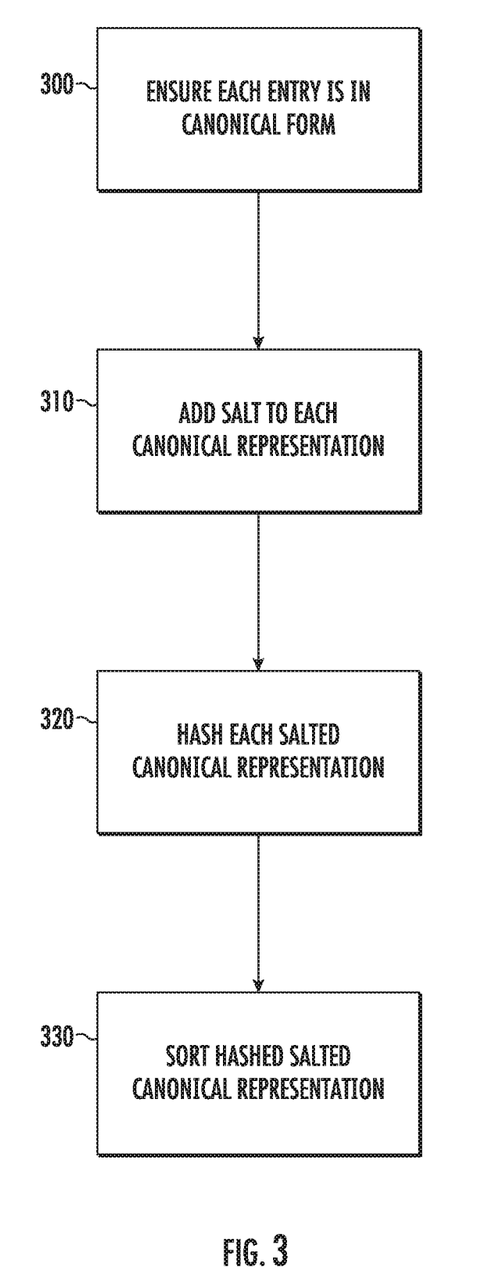
FIG. 3 shows a sequence to create the hashed proprietary database.

FIG. 3 shows a method that may be used to create the hashed proprietary database 80 that is provided to the retrosynthesis system 10. This method may be executed by providing an executable file to the customer's system 100. The executable file contains instructions, which when executed by the processing unit 120 on the customer's system 100, performs the functions described herein. In other words, the processes shown in FIG. 3 may be performed on the customer's system 100. In this way, the unencrypted customer's database 180 is never made available to the retrosynthesis system 10 or the software application. This executable file may be created by the retrosynthesis system 10 and transmitted to the customer's system 100, such as via download across the internet.

Each of the following processes is performed by the executable file. First, as shown in Process 300, each entry in the customer's database 180 is reviewed to ensure that it is in canonical form. This is necessary, as the comparison of hashed synthons can only be successful if each compound is denoted using only a single representation. After each entry has been reviewed and converted to canonical form, a salt may be added to each entry, as shown in Process 310. This salt may be unique to the particular customer and may be kept confidential. For example, in one embodiment, the executable file contains the unique salt, which is not made visible to the customer. The executable file and the software application use the same salt for a particular customer. In other embodiments, a salt may not be used. In these embodiments, Process 310 may be omitted. Next, as shown in Process 320, each entry, which is a canonical representation with a salt, is hashed. As noted above, the particular hashing algorithm is not limited by this disclosure. Each of these salted and hashed entries is then compiled into the proprietary database 80. Once this is complete, the proprietary database 80 may be made available to the software application, as the unencrypted contents are no longer accessible to the retrosynthesis system 10 or the software application.

Figure 4:
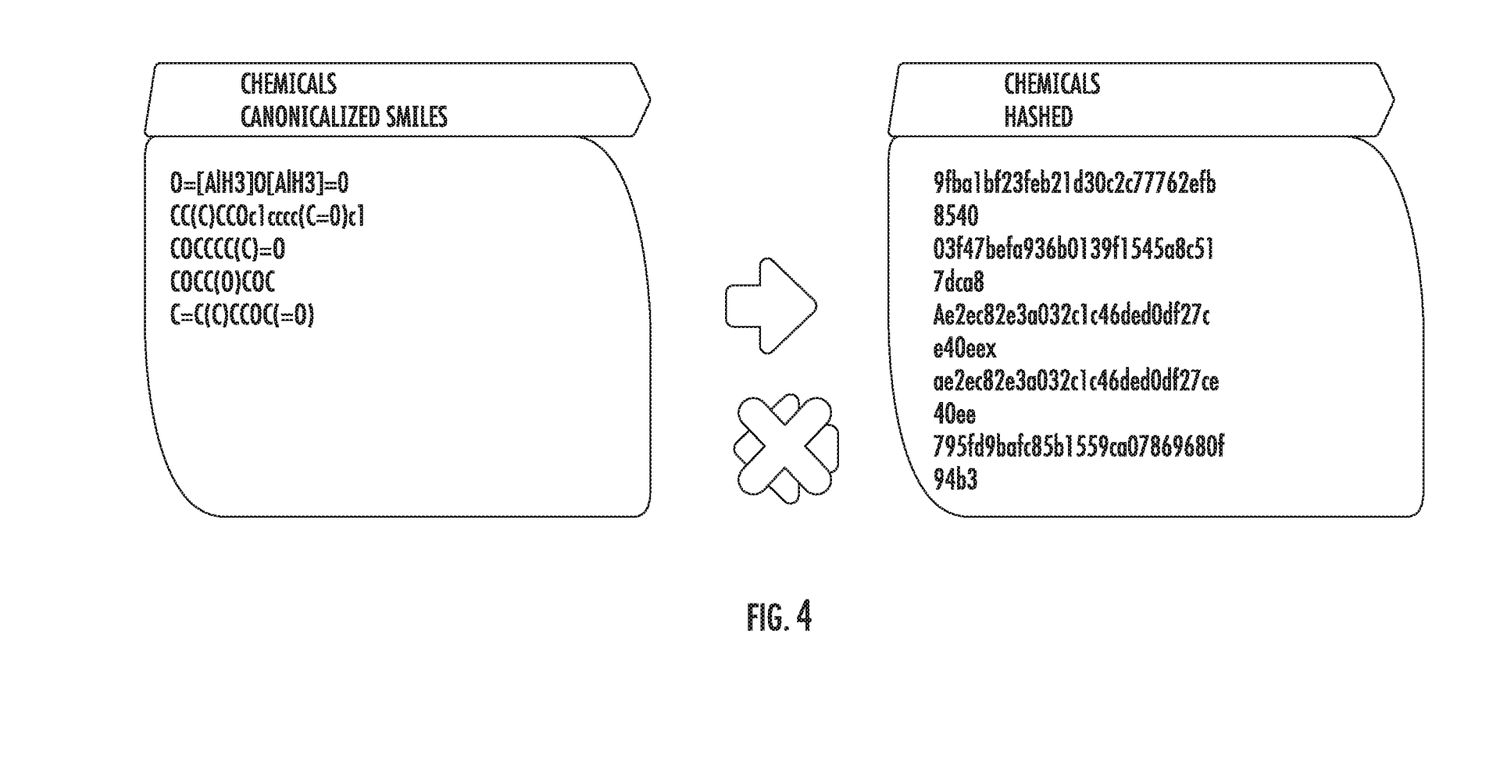
FIG. 4 shows the comparison of entries in the original database to the salted and hashed entries.

FIG. 4 shows several representative canonical SMILES strings and the resultant hashed values. Note that there is no way to recreate the canonical SMILES strings from the hashed values. Further, note that the hashed values do not provide any insight as to the original SMILES strings.

As an operational enhancement to FIG. 3, in certain embodiments, the salted and hashed canonical representations may be sorted, such as in alphabetical order, as shown in Process 330. This enhancement may reduce the time required for the software application to search the proprietary database 80 looking for a match.

Figure 5:
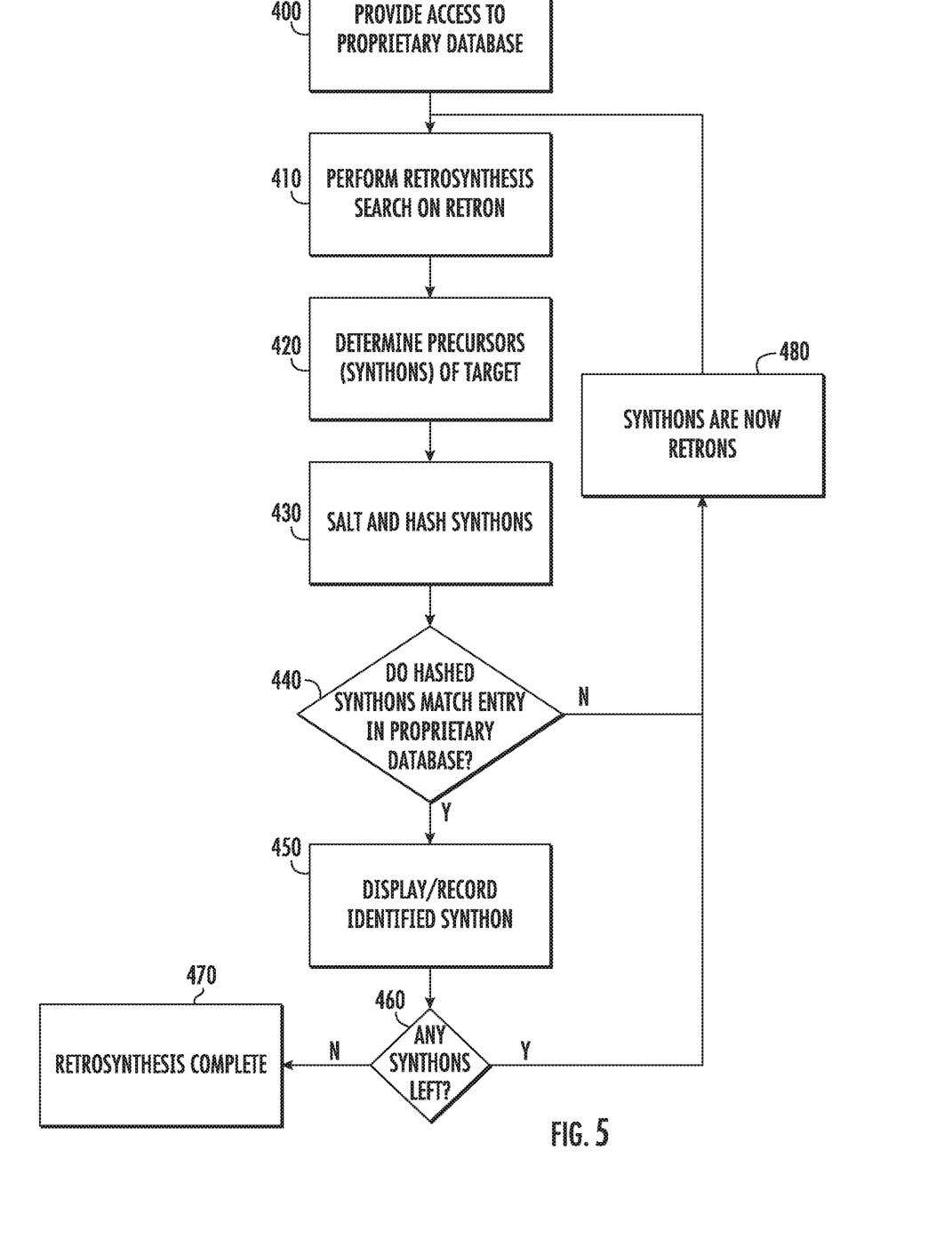
FIG. 5 shows a sequence to perform retrosynthesis using the hashed proprietary database.

Having described how the proprietary database 80 is created, the sequence used to perform the retrosynthesis for the customer will now be described. A representative flowchart of this sequence is shown in FIG. 5. First, as shown in Process 400, the proprietary database 80 is made available to the processing unit 20 of the retrosynthesis system 10. This may be achieved by uploading the proprietary database 80 to the retrosynthesis system 10, or by allowing the retrosynthesis system 10 to access the proprietary database 80 remotely.

Next, as shown in Process 410, the retrosynthetic search commences. Specifically, the matching reaction templates are applied, and the first generation of synthon sets is created. For the initial search, the retron is set to the target compound. For each candidate retron-to-synthon(s) transformation, $r \rightarrow s_1, s_2, \ldots, s_N$ (where r=t in the first generation), the synthons are identified, as shown in Process 420. As is well to those skilled in the art, a retron is a minimal molecular substructure that enables certain transformations. Also, as is well known, a synthon is a fragment of a compound that assists in the formation of a synthesis, derived from that target molecule.

Since the proprietary database 80 is hashed, in order to determine whether any of the synthons are in the proprietary database 80, it is necessary to perform the same operations on the synthons that were previously performed on the customer's database, as shown in Process 430. In other words, each synthon must be in canonical form. Each synthon is then salted (if this was performed to the proprietary database 80) using the same salt that was used in Process 310 in FIG. 3. Finally, the salted canonical representation of each synthon is hashed using the same hash algorithm that was used in Process 320 of FIG. 3.

Since the exact same transformation was performed on the synthons that was performed on the customer's database 180, the hashed synthons will only match to the exact same compound in the customer's database. Thus, as shown in Process 440, the hashed synthons are compared to the entries in the proprietary database 80. If a match is found, the synthon is recorded and/or displayed, as shown in Process 450. This path of the retrosynthesis is now complete, and this synthon does not need to undergo further analysis. The sequence continues by checking to see if there are other synthons that have not been matched to the proprietary database 80, as shown in Process 460. If there are other synthons that have not been identified yet, the retrosynthesis process continues. For example, the remaining synthons now are treated as the target molecule, as shown in Process 480. The retrosynthesis process then continues using these remaining synthons as the targets.

This process continues until all of the synthons have been found in the proprietary database 80, as shown in Process 470. The resulting synthesis paths are then provided to the customer, such as, diplaying a result on the display device 140 associated with the customer's system 100. Alternatively, the resulting synthesis paths may be provided to the customer via a text file, email, or other means.

Figure 6:
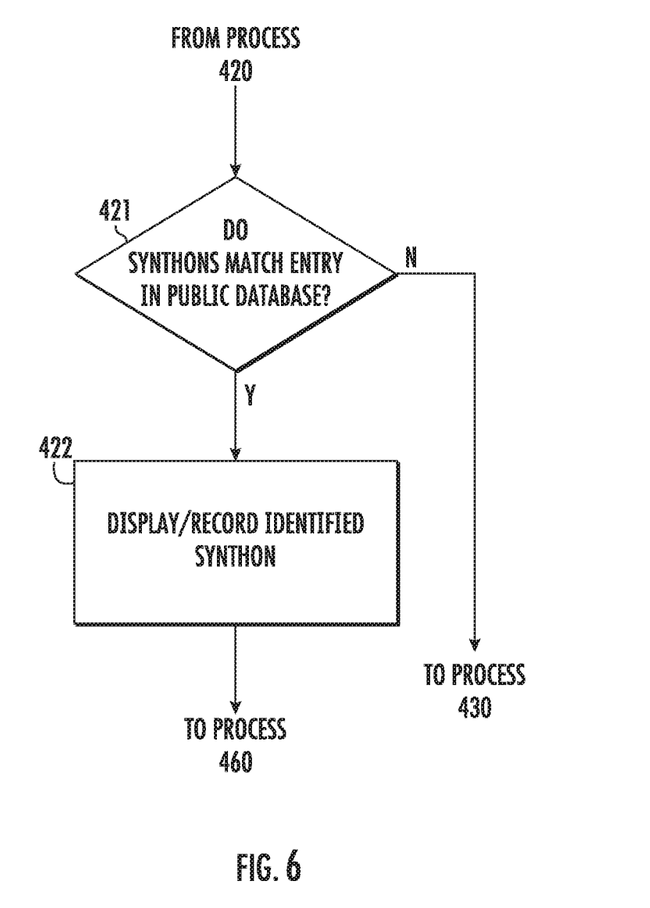
FIG. 6 shows an enhancement to the sequence of FIG. 5 to utilize a second data store.

FIG. 6 shows an enhancement to the sequence of FIG. 5. Specifically, in certain embodiments, the retrosynthesis system 10 may include both the proprietary database 80 and a data store 50 of commercially available compounds and substances. While the proprietary database 80 is salted and hashed, the data store 50 may not be. Thus, in certain embodiments, the sequence includes Processes 421 and 422, which follow Process 420. As shown in Process 421, the synthons may be compared to the entries in the data store 50. These comparisons are made before the synthons are hashed. If any of the synthons match an entry in the data store 50, that synthon is displayed and/or recorded, as shown in Process 422. The sequence then proceeds to Process 460. If the synthon does not match any of the entries in the data store 50, the sequence continues with Process 430. In this way, both commercially available substances and proprietary substances may be included in the search algorithm.

Figure 7:
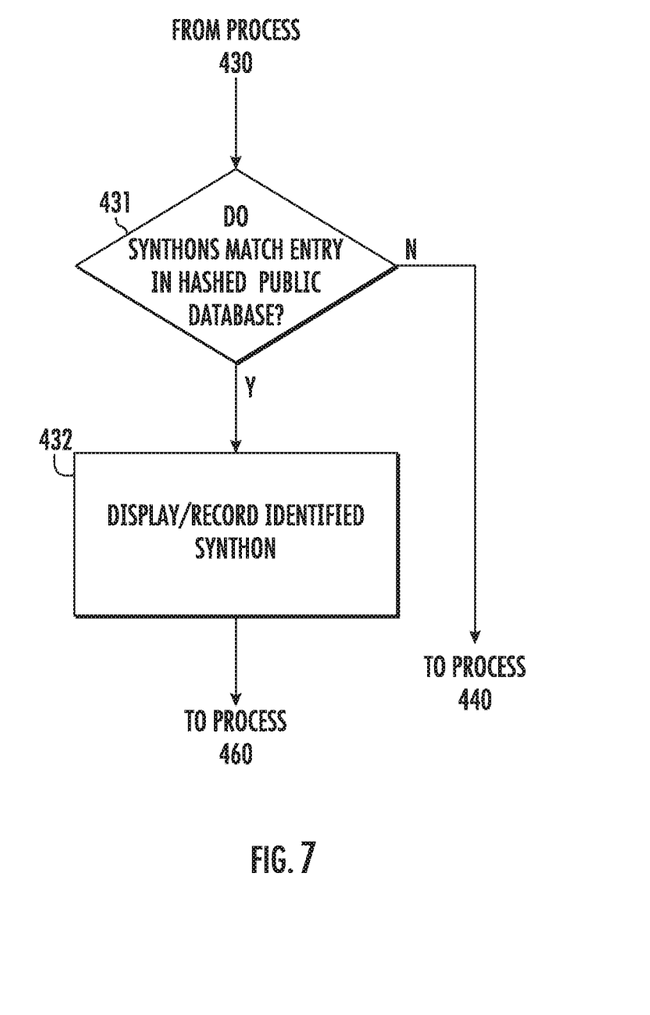
FIG. 7 shows a variation of the process shown in FIG. 6.

In a variation of FIG. 6, shown in FIG. 7, the data store 50 is also salted and hashed using the same parameters as the proprietary database 80. Thus, after the synthons have been salted and hashed, as shown in Process 430, the salted hashed synthons are then compared to the entries in the hashed public database, as shown in Process 431. If a match is found, the synthon is displayed and/or recorded, as shown in Process 432. The sequence would then continue with Process 460. If a match is not found, the sequence would then proceed to Process 440, where the hashed synthon is compared to entries in the proprietary database 80.

While the above description discloses that the executable file provides the unique salt to the customer, other embodiments are also possible. For example, in another embodiment, the executable file may allow the customer to enter a password which will serve as the salt. This password is then used by the executable file to salt the customer's database 180 to create the proprietary database 80, as shown in Process 310. Further, this password is transmitted to the retrosynthesis system 10 so that the same password is used to perform the salt process shown in Process 430.

Thus, the present disclosure describes a system, method and software application that allows the user to utilize a propriety database without allowing the software application to access the contents of that proprietary database. This may reduce customer's uneasiness of providing their confidential information to another party, while still allowing them to make use of this software application.

Further, the use of a unique salt for each customer also increases the security of the customer's database. Specifically, if a salt is not used, it may be possible to compare the proprietary databases of multiple customers to determine commonality. However, the use of a salt implies that the same compound, in two different customer's proprietary databases, will not have the same final hash, thus making it impossible to make comparisons between databases.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A method of performing retrosynthesis on a target compound, comprising:
    setting the target compound to a retron;
    performing a first retrosynthesis search on the retron to find a set of synthons;
    hashing each synthon of the set of synthons;
    comparing each hashed synthon to entries in a proprietary database, where the entries in the proprietary database are hashed using same hash algorithm;
    if the comparison succeeds, recording and/or displaying the synthon; and
    if the comparison fails, setting the set of synthons to the retron and repeating the performing, hashing, and comparing steps.

2. The method of claim 1, wherein the set of synthons are salted prior to being hashed and the entries in the proprietary database are salted using the same salt.

3. The method of claim 2, wherein the salt is unique for each customer.

4. The method of claim 1, wherein the set of synthons are also compared to entries in a public database.

5. The method of claim 4, wherein the entries in the public database are not hashed.

6. The method of claim 4, wherein the entries in the public database are hashed using the same hash algorithm as the proprietary database.

7. The method of claim 1, wherein an executable file is used to create the proprietary database.

8. The method of claim 7, wherein the executable file comprises instructions, which when executed by a processing unit, allow the processing unit to:
    convert all entries in a customer's database to canonical form;
    hash each entry after conversion to canonical form; and
    store the hashed entries in the proprietary database.

9. The method of claim 8, wherein the executable file further includes a unique salt and comprises instructions, which when executed by the processing unit, allow the processing unit to:

salt each entry in canonical format prior to the hash.

10. The method of claim 8, wherein the executable file further comprises instructions, which when executed by the processing unit, allow the processing unit to:

request a password from a customer;
utilize the password as a salt; and
salt each entry in canonical format prior to the hash.

11. The method of claim 8, wherein each entry in the customer's database is in SMILES notation.

12. The method of claim 8, wherein each entry in the customer's database is in InChI notation.

13. The method of claim 8, wherein each entry in the customer's database is in InChI-Keys notation.

14. A software program, disposed on a non-transitory storage media, the software program comprising instructions, which when executed by a processing unit perform retrosynthesis on a target compound, by:

setting the target compound to a retron;
performing a first retrosynthesis search on the retron to find a set of synthons;
hashing each synthon of the set of synthons;
comparing each hashed synthon to entries in a proprietary database, where the entries in the proprietary database are hashed using same hash algorithm;
if the comparison succeeds, recording and/or displaying the synthon; and
if the comparison fails, setting the set of synthons to the retron and repeating the performing, hashing, and comparing steps.

15. The software program of claim 14, wherein the software program further comprises instructions to:

salt the set of synthons prior to being hashed; wherein the entries in the proprietary database are salted using the same salt.

16. The software program of claim 14, wherein the software program further comprises instructions to:

compare the set of synthons to entries in a public database.

17. The software program of claim 16, wherein the public database is not hashed.

18. The software program of claim 16, wherein the entries in the public database are hashed using the same hash algorithm as the proprietary database.

* * * * *